US011172820B2

(12) United States Patent
Sugo et al.

(10) Patent No.: US 11,172,820 B2
(45) Date of Patent: Nov. 16, 2021

(54) PHYSIOLOGICAL INFORMATION PROCESSING APPARATUS, PHYSIOLOGICAL INFORMATION PROCESSING METHOD, AND STORAGE MEDIUM

(71) Applicant: NIHON KOHDEN CORPORATION, Tokyo (JP)

(72) Inventors: Yoshihiro Sugo, Tokorozawa (JP); Yoshiharu Harada, Tokorozawa (JP); Tomoyuki Sakai, Tokorozawa (JP); Mami Sakai, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 75 days.

(21) Appl. No.: 16/393,307

(22) Filed: Apr. 24, 2019

(65) Prior Publication Data

US 2019/0343387 A1 Nov. 14, 2019

(30) Foreign Application Priority Data

May 9, 2018 (JP) .............................. JP2018-090625

(51) Int. Cl.
*A61B 5/02* (2006.01)
*A61B 5/00* (2006.01)
(Continued)

(52) U.S. Cl.
CPC .......... *A61B 5/0022* (2013.01); *A61B 5/0006* (2013.01); *A61B 5/0205* (2013.01); *A61B 5/02416* (2013.01); *A61B 5/02438* (2013.01); *A61B 5/742* (2013.01); *A61B 5/026* (2013.01); *A61B 5/0245* (2013.01);
(Continued)

(58) Field of Classification Search
CPC ...... G16H 20/17; G16H 40/63; A61B 5/0022; A61B 5/0205; A61B 5/0006; A61B 5/02416; A61B 5/02438; A61B 5/742; A61B 5/0245; A61B 5/0432; A61B 5/6898; A61B 5/6824; A61B 5/6814; A61B 5/681; A61B 5/026; A61B 5/02116;
(Continued)

(56) References Cited

U.S. PATENT DOCUMENTS

2013/0096403 A1* 4/2013 Dacso ................ A61B 5/14551
600/324
2014/0058229 A1 2/2014 Su et al.
(Continued)

FOREIGN PATENT DOCUMENTS

WO 2014031847 A1 2/2014

*Primary Examiner* — Amanda K Hulbert
*Assistant Examiner* — Natasha Patel
(74) *Attorney, Agent, or Firm* — Pearne & Gordon LLP (57) ABSTRACT

A physiological information processing method includes: acquiring electrocardiogram data from a subject; acquiring pulse wave data from the subject; measuring a plurality of RR intervals based on the acquired electrocardiogram data; measuring a plurality of pulse wave transit times based on the acquired electrocardiogram data and the acquired pulse wave data; calculating, based on the measured RR intervals and the measured pulse wave transit times during a given time period, a parameter related to correlation between the measured RR intervals and the measured pulse wave transit times; and outputting the calculated parameter.

18 Claims, 3 Drawing Sheets

(51) Int. Cl.
  *A61B 5/0205*   (2006.01)
  *A61B 5/024*    (2006.01)
  *A61B 5/0245*       (2006.01)
  *A61B 5/026*        (2006.01)
  *A61B 5/021*        (2006.01)
  *A61B 5/333*        (2021.01)

(52) U.S. Cl.
  CPC ........... *A61B 5/02116* (2013.01); *A61B 5/333* (2021.01); *A61B 5/681* (2013.01); *A61B 5/6814* (2013.01); *A61B 5/6824* (2013.01); *A61B 5/6898* (2013.01)

(58) Field of Classification Search
  CPC ..... A61B 5/4875; A61B 5/746; A61B 5/0456; A61B 5/7246
  See application file for complete search history.

(56) References Cited

U.S. PATENT DOCUMENTS

| | | | |
|---|---|---|---|
| 2015/0265196 A1 | 9/2015 | Su et al. | |
| 2015/0305632 A1* | 10/2015 | Najarian | A61B 5/7207 600/301 |
| 2017/0049352 A1* | 2/2017 | Mirov | A61B 5/0533 |
| 2018/0085011 A1* | 3/2018 | Ma | A61B 5/318 |

* cited by examiner

PHYSIOLOGICAL INFORMATION PROCESSING APPARATUS, PHYSIOLOGICAL INFORMATION PROCESSING METHOD, AND STORAGE MEDIUM

CROSS REFERENCE TO RELATED APPLICATION

This application is based on Japanese Patent Application No. 2018-090625 filed on May 9, 2018, the contents of which are incorporated herein by reference.

BACKGROUND

The presently disclosed subject matter relates to a physiological information processing apparatus and a physiological information processing method. The presently disclosed subject matter further relates to a program causing a computer to execute the physiological information processing method, and a computer readable storage medium storing the program.

US 2014/0058229 A discloses a method of detecting a fluid responsiveness of a patient. The method includes: determining amplitude modulation AM and/or frequency modulation FM of a photoplethysmogram (PPG) signal; determining baseline modulation BM of the PPG signal; determining a ratio of the amplitude modulation AM to the baseline modulation BM or that of the frequency modulation FM to the baseline modulation BM; and determining an index of a fluid responsiveness of the patient based on the determined ratio.

Particularly, US 2014/0058229 A discloses that, in the case where the determined ratio exceeds a given threshold, an additional fluid administration to the patient is performed, and, in the case where the determined ratio is smaller than the given threshold, the additional fluid administration to the patient is stopped.

In the disclosure of US 2014/0058229, the determination of whether an additional fluid is to be administered to the patient or not (hereinafter, the determination is referred to as the fluid administration determination) is performed based on an index value which is calculated from the PPG signal (i.e., pulse wave data) indicating that the pulsation from the heart existing in the center reaches the periphery. On the other hand, in order to further enhance the reliability of the fluid administration determination, preferably, the fluid administration determination is performed based on, in addition to the PPG signal, an index value which is calculated from physiological data that directly reflect the state of the heart existing in the center. However, the larger the kinds of physiological data to be acquired, the larger the kinds of physiological sensors. Therefore, the cost for performing the fluid administration determination is increased. In this respect, during a surgical operation, two non-invasive sensors, i.e., a pulse wave sensor for acquiring pulse wave data and an electrocardiogram sensor for acquiring electrocardiogram data are usually used, and therefore it is considered that the fluid administration determination to be performed by a medical person may be supported by using the two different physiological data, i.e., pulse wave data, and electrocardiogram data that directly reflect the state of the heart existing in the center.

The presently disclosed subject matter provides a physiological information processing apparatus and method which may support the fluid administration determination to be performed by a medical person by means of two different physiological data, i.e., pulse wave data, and electrocardiogram data. The presently disclosed subject matter further provides a program for causing a computer to execute the physiological information processing method, and a computer readable storage medium storing the program.

SUMMARY

According to an aspect of the presently disclosed subject matter, a physiological information processing method includes:
acquiring electrocardiogram data from a subject;
acquiring pulse wave data from the subject;
measuring a plurality of RR intervals based on the acquired electrocardiogram data;
measuring a plurality of pulse wave transit times based on the acquired electrocardiogram data and the acquired pulse wave data;
calculating, based on the measured RR intervals and the measured pulse wave transit times during a given time period, a parameter related to correlation between the measured RR intervals and the measured pulse wave transit times; and
outputting the calculated parameter.

According to another aspect of the presently disclosed subject matter, a computer readable storage medium stores a program causing a computer to execute a process for processing physiological information. The process includes:
acquiring electrocardiogram data from a subject;
acquiring pulse wave data from the subject;
measuring a plurality of RR intervals based on the acquired electrocardiogram data;
measuring a plurality of pulse wave transit times based on the acquired electrocardiogram data and the acquired pulse wave data;
calculating, based on the measured RR intervals and the measured pulse wave transit times during a given time period, a parameter related to correlation between the measured RR intervals and the measured pulse wave transit times; and
outputting the calculated parameter.

According to another aspect of the presently disclosed subject matter, a physiological information processing apparatus includes:
a processor; and
a memory that stores computer readable instructions,
wherein, when the computer readable instructions are executed by the processor, the physiological information processing apparatus performs:
acquiring electrocardiogram data from a subject;
acquiring pulse wave data from the subject;
measuring a plurality of RR intervals based on the acquired electrocardiogram data;
measuring a plurality of pulse wave transit times based on the acquired electrocardiogram data and the acquired pulse wave data;
calculating, based on the measured RR intervals and the measured pulse wave transit times during a given time period, a parameter related to correlation between the measured RR intervals and the measured pulse wave transit times; and
outputting the calculated parameter.

According to the presently disclosed subject matter, it is possible to provide a physiological information processing apparatus and method which may support the fluid administration determination to be performed by a medical person by means of two different physiological data, i.e., pulse wave data, and electrocardiogram data. Moreover, it is possible to provide a program for causing a computer to execute the physiological information processing method, and a computer readable storage medium storing the program.

DETAILED DESCRIPTION OF EMBODIMENTS

Hereinafter, an embodiment will be described with reference to the drawings. Initially, the hardware configuration of a physiological information processing apparatus 1 of an embodiment of the presently disclosed subject matter (hereinafter, referred to simply as the embodiment) will be described.

Figure 1:
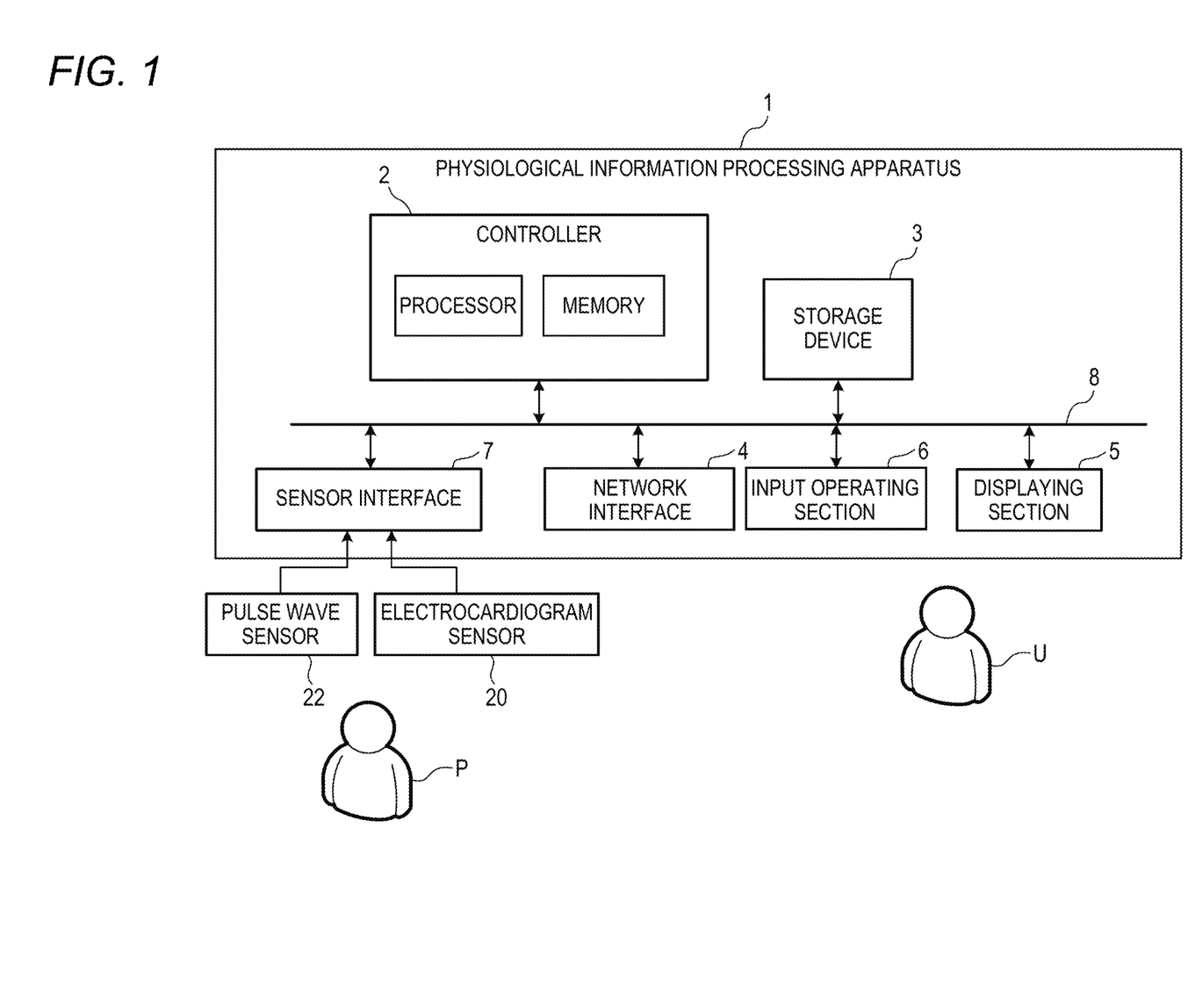
FIG. 1 illustrates an example of the hardware configuration of a physiological information processing apparatus of an embodiment of the presently disclosed subject matter.

FIG. 1 is a diagram illustrating an example of the hardware configuration of the physiological information processing apparatus 1 of the embodiment. As illustrated in FIG. 1, the physiological information processing apparatus 1 (hereinafter, referred to simply as the processing apparatus 1) includes a controller 2, a storage device 3, a network interface 4, a displaying section 5, an input operating section 6, and a sensor interface 7. These components are communicably connected to one another via a bus 8.

The processing apparatus 1 may be an apparatus (a patient monitor or the like) dedicated to display of a trend graph of vital signs of a subject P, or, for example, a personal computer, a workstation, a smart phone, a tablet, or a wearable device (such as a smart watch or an AR glass) which is to be attached to the body (such as the arm or the head) of a medical person U.

The controller 2 may include one or more memory and one or more processor. The one or more memory is configured so as to store computer readable instructions (programs), and may be configured by, for example, a ROM (Read Only Memory) which stores various programs and the like, and a RAM (Random Access Memory) having a plurality of work areas in which various programs to be executed by the processor, and the like are stored. Alternatively, the memory may be configured by a flash memory or the like. For example, the one or more processor is a CPU (Central Processing Unit), an MPU (Micro Processing Unit), and/or a GPU (Graphics Processing Unit). The CPU may be configured by a plurality of CPU cores. The GPU may be configured by a plurality of GPU cores. The one or more processor may be configured so as to develop a designated one of the various programs installed in the storage device 3 or the ROM, in the RAM, and execute various processes in cooperation with the RAM.

The one or more processor may develop a physiological information processing program which will be described later, in the RAM, and execute the program in cooperation with the RAM, thereby enabling the controller 2 to control various operations of the processing apparatus 1. The physiological information processing program will be described in detail later.

For example, the storage device 3 is a storage device such as an HDD (Hard Disk Drive), an SSD (Solid State Drive), or a flash memory, and configured so as to store programs and various data. The physiological information processing program may be incorporated in the storage device 3. The storage device 3 may store physiological information data such as electrocardiogram data, and pulse wave data of the subject P. For example, electrocardiogram data which are acquired by an electrocardiogram sensor 20 may be stored in the storage device 3 through the sensor interface 7.

The network interface 4 is configured so as to connect the processing apparatus 1 to a communication network. Specifically, the network interface 4 may include various wired connection terminals for communicating with an external apparatus such as a server through the communication network. The network interface 4 may further include various processing circuits, antenna, and the like for wirelessly communicating with an access point. For example, the standard of wireless communication between the access point and the processing apparatus 1 is the Wi-Fi (registered trademark), the Bluetooth (registered trademark), the ZigBee (registered trademark), the LPWA, or a fifth generation mobile communication system (5G). The communication network is a LAN (Local Area Network), a WAN (Wide Area Network), the Internet, or the like. For example, the physiological information processing program and physiological information data may be acquired from the server placed in the communication network, through the network interface 4.

The displaying section 5 may be a display device such as a liquid crystal display or an organic EL display, or that such as a transmission or non-transmission head mounted display which is to be attached to the head of the operator. Alternatively, the displaying section 5 may be a projector device which projects an image onto a screen.

The input operating section 6 is configured so as to receive an input operation performed by the medical person U who operates the processing apparatus 1, and produce an instruction signal corresponding to the input operation. For example, the input operating section 6 is configured by a touch panel which is placed overlappingly on the displaying section 5, operation buttons which are attached to the housing, or a mouse and/or a keyboard. The instruction signal which is produced by the input operating section 6 is transmitted to the controller 2 via the bus 8, and then the controller 2 executes a given operation according to the instruction signal.

The sensor interface 7 is an interface which enables vital sensors such as the electrocardiogram sensor 20 and a pulse wave sensor 22 to be communicably connected to the processing apparatus 1. The sensor interface 7 may include input terminals to which the physiological data output from these vital sensors are input. The input terminals may be physically connected to connectors of the vital sensors. The sensor interface 7 may further include various processing circuits, antenna, and the like for wirelessly communicating with the vital sensors.

The electrocardiogram sensor 20 is configured so as to acquire electrocardiogram data indicating the electrocardiogram waveform of the subject P. The pulse wave sensor 22 is configured so as to acquire pulse wave data indicating the pulse wave of the subject P.

Figure 2:
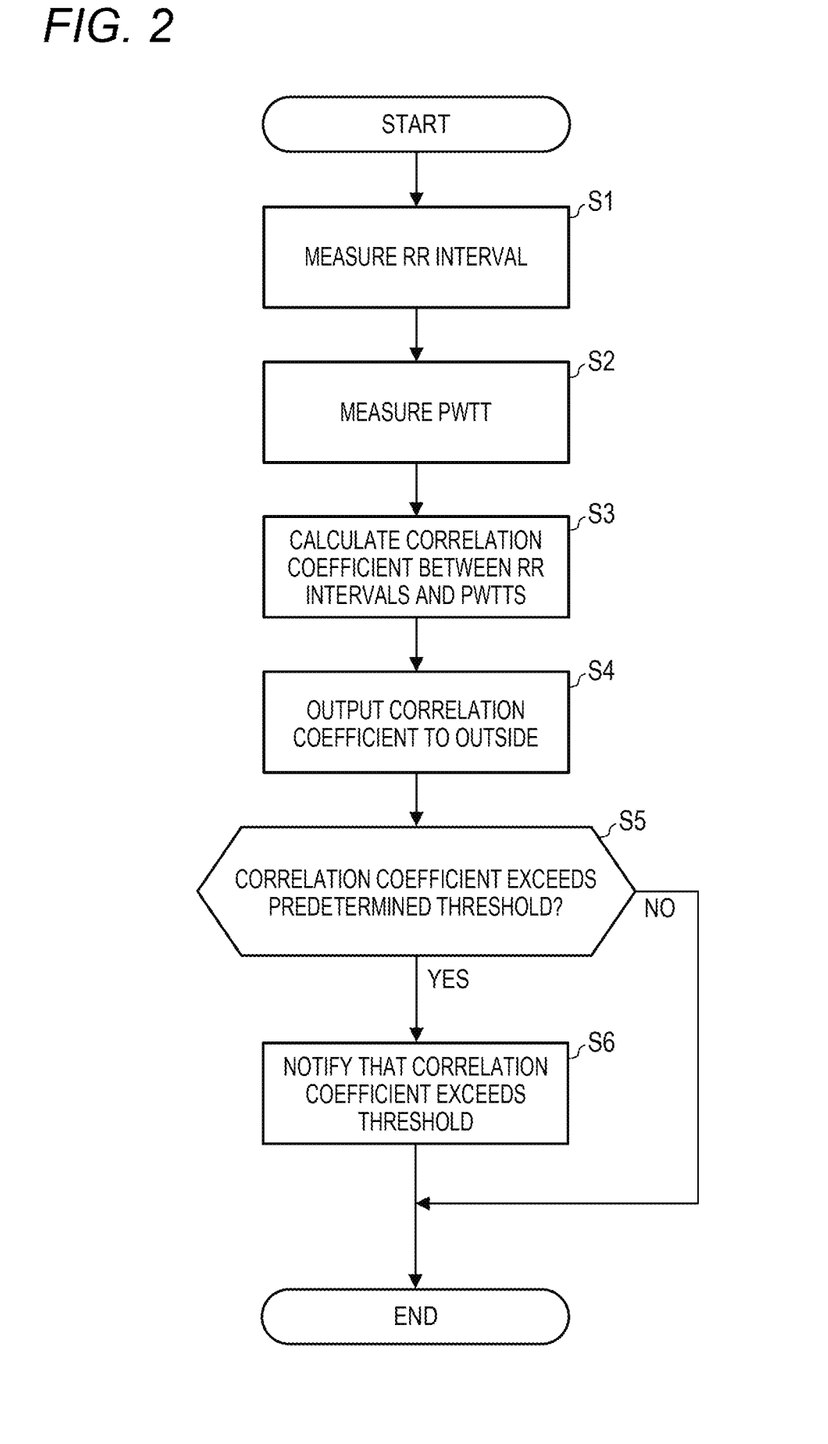
FIG. 2 is a flowchart for explaining an example of a physiological information processing method of the embodiment of the presently disclosed subject matter.

Next, a physiological information processing method of the embodiment will be described with reference to FIG. 2. FIG. 2 is a flowchart illustrating an example of the physiological information processing method of the embodiment. As illustrated in FIG. 2, the controller 2 firstly acquires the electrocardiogram data of the subject P from the electrocardiogram sensor 20, and the pulse wave data of the subject P from the pulse wave sensor 22. Next, the controller 2 identifies a plurality of RR intervals indicating the time intervals between adjacent R waves, based on the acquired electrocardiogram data (step S1).

Next, the controller 2 measures, in step S2, a plurality of pulse wave transit times (hereinafter, referred to as PWTTs) based on the electrocardiogram data and the pulse wave data. The PWTT means a time interval from the peak point of a given R wave of an electrocardiogram to the rising point of a given pulse waveform which appears next to the given R wave. Therefore, the controller 2 specifies the time of the peak point of the given R wave from the electrocardiogram data, and further specifies that of the rising point of the given pulse waveform which appears next to the given R wave, from the pulse wave data. Next, the controller 2 calculates the time interval between the time of the rising point of the given pulse waveform and that of the peak point of the given R wave, thereby measuring the PWTT.

Based on a plurality of RR intervals and plurality of PWTTs during a given time period T, next, the controller 2 calculates a correlation coefficient r between the plurality of RR intervals and the plurality of PWTTs (step S3). Here, the correlation coefficient r is an example of the parameter related to correlation between the plurality of RR intervals and the plurality of PWTTs. For example, the given time period T is a time period between times t1 and t2 (<t1) which are earlier than the current time tc.

Figure 3:
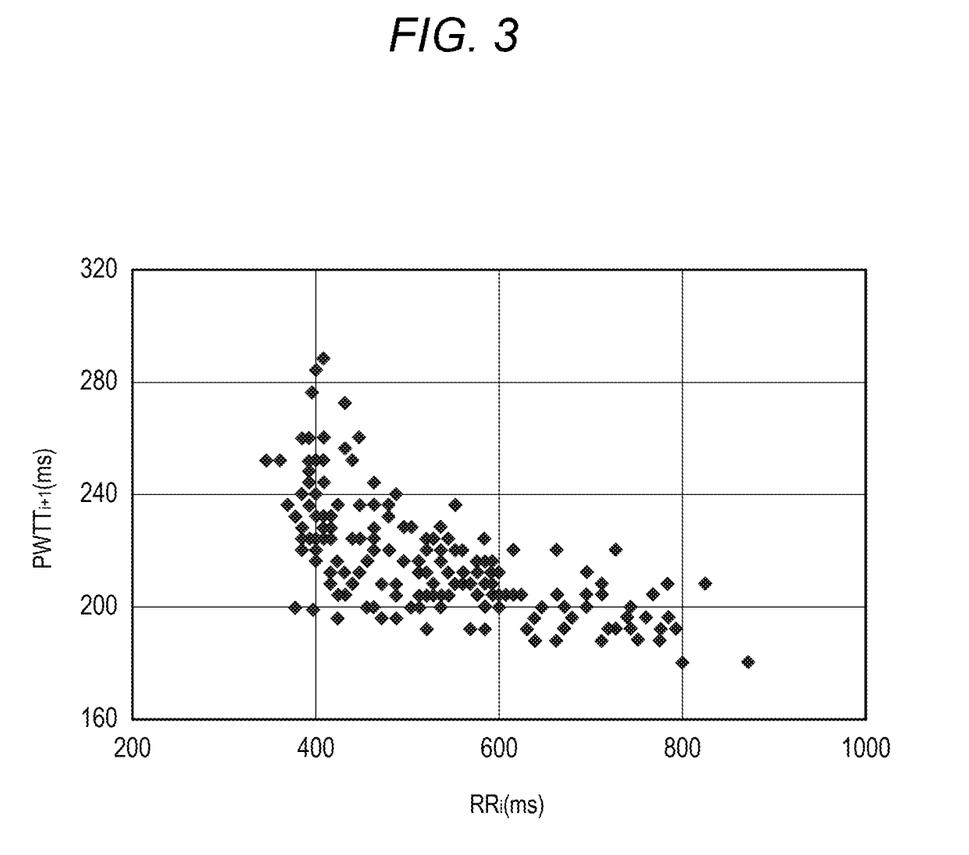
FIG. 3 illustrates an example of relationships between a plurality of RR intervals and a plurality of pulse wave transit times.

Specifically, the controller 2 calculates the correlation coefficient r based on data (hereinafter, referred to as RR/PWTT data) configured by a plurality of RR intervals $RR_i$ (i is a natural number) during the given time period T, and a plurality of $PWTT_{i+1}$ each correlated to one of the plurality of RR intervals $RR_i$. In the case where an n number of R waves and an n number of pulse waveforms exist in the electrocardiogram data and pulse wave data during the given time period T, for example, an i-th (i=1, 2, . . . , n-1) RR interval $RR_i$ indicates the time interval between the peak point of an i-th R wave and that of an (i+1)-th R wave. By contrast, $PWTT_i$ which is an i-th PWTT indicates the time interval between the peak point of an i-th R wave and the rising point of an i-th pulse waveform. In RR/PWTT data configured by a plurality of $RR_i$ and a plurality of $PWTT_{i+1}$, $RR_i$ is correlated with $PWTT_{i+1}$. In this way, RR1 is correlated with PWTT2, and $RR_{n-1}$ is correlated with $PWTT_n$. The table below shows an example of RR/PWTT data. FIG. 3 illustrates an example of relationships between a plurality of RR intervals and a plurality of PWTTs.

TABLE 1

Example of RR/PWTT data

| i | $RR_i$ | $PWTT_{i+1}$ |
|---|--------|--------------|
| 1 | 500    | 330          |
| 2 | 510    | 225          |
| 3 | ...    |              |
| ... | ...  | ...          |

The controller 2 may calculate the correlation coefficient r based on Expression (1) below.

$$r = \frac{S_{RR/PWTT}}{S_{RR}S_{PWTT}} \quad (1)$$

-continued
$$= \frac{\frac{1}{n-1}\sum_{i=1}^{n-1}(RR_i - \overline{RR})(PWTT_{i+1} - \overline{PWTT})}{\sqrt{\frac{1}{n-1}\sum_{i=1}^{n-1}(RR_i - \overline{RR})^2}\sqrt{\frac{1}{n-1}\sum_{i=1}^{n-1}(PWTT_{i+1} - \overline{PWTT})^2}}$$

In the expression, SSRR indicates the standard deviation of $RR_i$, SPWTT indicates the standard deviation of $PWTT_{i+1}$, and SRR/PWTT indicates the covariance between $RR_i$ and $PWTT_{i+1}$.

In step S4, next, the controller 2 outputs the calculated correlation coefficient r to the outside. For example, the controller 2 causes the correlation coefficient r to be displayed on the displaying section 5, thereby visually presenting the correlation coefficient r to the operator U. In this case, the controller 2 may display a graph such as illustrated in FIG. 3 indicating relationships between a plurality of RR intervals and a plurality of PWTTs, together with the current value of the correlation coefficient r, on the displaying section 5. Moreover, the controller 2 may present the correlation coefficient r through a printer which is not illustrated, to the operator U. Alternatively, the controller 2 may audibly present the correlation coefficient r through a speaker which is not illustrated, to the operator U.

In step S5, next, the controller 2 determines whether the correlation coefficient r exceeds a given threshold $r_{th}$ or not. Here, the given threshold $r_{th}$ is, for example, −0.2. The given threshold $r_{th}$ may be appropriately set on the side of a medical facility. If the determination result of step S5 is YES, the process proceeds to step S6. If the determination result of step S5 is NO, the process is ended.

If the determination result of step S5 is YES, the controller 2 notifies the operator U that the correlation coefficient r exceeds the given threshold $r_{th}$ (step S6). For example, the controller 2 may change the visual mode of the display screen of the displaying section 5 on which the correlation coefficient r is displayed. More specifically, the controller 2 may cause the correlation coefficient r displayed on the display screen, to blink, or the display color of the correlation coefficient r to be changed. Alternatively, a warning symbol indicating that the correlation coefficient r exceeds the given threshold $r_{th}$ may be displayed on the display screen. Moreover, the controller 2 may audibly present a warning sound or guidance indicating that the correlation coefficient r exceeds the given threshold $r_{th}$, to the operator U.

The series of processes of the physiological information processing method of the embodiment is executed as described above. The processes illustrated in FIG. 2 may be repeatedly executed every given time period (for example, every 1 second).

When the RR interval is reduced, usually, the stroke volume is reduced. When the RR interval is increased, the stroke volume is increased. In this way, there is a positive correlation between the RR interval and the stroke volume. When the stroke volume is reduced, moreover, the PWTT is increased. When the stroke volume is increased, the PWTT is reduced. In this way, there is a negative correlation between the stroke volume and the PWTT. That is, there is a positive correlation between the RR interval and the stroke volume, and there is a negative correlation between the stroke volume and the PWTT. Consequently, there is a negative correlation between the RR interval and the PWTT.

The negative correlation between the RR interval and the PWTT depends on the amount of blood flowing into the heart of the subject P. When the amount of blood flowing into the heart is small, namely, the negative correlation between the RR interval and the PWTT remarkably appears, and, when the amount of blood flowing into the heart is large, the negative correlation between the RR interval and the PWTT does not appear.

It is considered that, in the case where a negative correlation strongly appears between the RR interval and the PWTT (namely, in the case where the correlation coefficient r is smaller than the given threshold $r_{th}$), the amount of blood flowing into the heart of the subject P is small. Therefore, it is possible to determine that an additional fluid is to be administered to the subject P. By contrast, it is considered that, in the case where a negative correlation does not appear between the RR interval and the PWTT (namely, in the case where the correlation coefficient r is equal to or larger than the given threshold $r_{th}$), the amount of blood flowing into the heart is large. Therefore, it is possible to determine that an additional fluid is not to be administered to the subject P.

As described above, the inventors of the invention have newly found that, when the correlation between the RR interval and the PWTT is focused, the fluid administration determination to be performed by a medical person may be supported. In the embodiment, moreover, the correlation coefficient r between a plurality of RR intervals and the plurality of PWTTs is calculated, and then the calculated correlation coefficient r is presented to the operator U. When the operator (medical person) U checks the correlation coefficient r, therefore, the operator may determine whether an additional fluid is to be administered to the subject P or not. Therefore, it is possible to provide the physiological information processing method and processing apparatus 1 which may support the fluid administration determination to be performed by the operator U by means of two different physiological data, i.e., pulse wave data, and electrocardiogram data.

According to the embodiment, moreover, the situation where the correlation coefficient r exceeds the given threshold $r_{th}$ is notified to the operator U. Therefore, the operator U may know surely and quickly, from the notification, the situation where the correlation coefficient r exceeds the given threshold $r_{th}$, and hence promptly determine that an additional fluid is not to be administered to the subject P.

Although, in the embodiment, the correlation coefficient r is calculated as an example of the parameter related to correlation between the plurality of RR intervals and the plurality of PWTTs, the gradient a of a regression line indicating correlation between the plurality of RR intervals and the plurality of PWTTs may be calculated in place of the correlation coefficient r. In the case where a plurality of RR intervals are not distributed in a normal distribution, particularly, the controller 2 may use the gradient a of a regression line as the parameter related to correlation between the plurality of RR intervals and the plurality of PWTTs. For example, the controller 2 may calculate the gradient a of a regression line based on following Expression (2).

$$a = \frac{S_{RR/PWTT}}{S_{RR}^2} \quad (2)$$

$$= \frac{\sum_{i=1}^{n-1}(RR_i - \overline{RR})(PWTT_{i+1} - \overline{PWTT})}{\sum_{i=1}^{n-1}(RR_i - \overline{RR})^2}$$

In the case where the gradient a is used, the controller 2 determines in step S5 whether the gradient exceeds a given threshold $a_{th}$ or not. Here, the given threshold $a_{th}$ is −0.025. The given threshold $a_{th}$ may be appropriately set on the side of the medical facility. The CCC (Concordance Correlation Coefficient) may be used as the parameter related to correlation between the plurality of RR intervals and the plurality of PWTTs. In the case where changes of RR intervals and PWTTs are small, and influences of a physiological change and an artifact of RR intervals and PWTTs are to be eliminated, particularly, the CCC may be used.

Although, in the embodiment, the situation where the correlation coefficient r exceeds the given threshold $r_{th}$ is notified to the operator U, the embodiment is not limited to this. When the correlation coefficient r exceeds the given threshold $r_{th}$, for example, the situation where the correlation coefficient r exceeds the given threshold $r_{th}$ is notified to the operator U, and, together with the notification (or in place of the notification), a fluid administration control circuit (not shown) may be controlled so as to automatically stop the fluid administration to the subject P. Here, the fluid administration control circuit is configured so as to control the amount of the fluid to be administered to the subject P. The fluid administration control circuit is electrically connected to a fluid administration adjustment mechanism which is configured so as to adjust the amount of the fluid to be administered to the subject P. When the correlation coefficient r exceeds the given threshold $r_{th}$, for example, the controller 2 produces a stop instruction signal for instructing the stop of fluid administration, and then transmits the stop instruction signal to the fluid administration control circuit. In response to reception of the stop instruction signal, the fluid administration control circuit controls the driving of the fluid administration adjustment mechanism so as not to administer the fluid to the subject P.

In order to realize the processing apparatus 1 of the embodiment by using software, the physiological information processing program may be pre-installed in the storage device 3 or the ROM. Alternatively, the physiological information processing program may be stored on a computer readable storage medium such as a magnetic disk (such as an HDD or a floppy disk), an optical disk (such as a CD-ROM, a DVD-ROM, or a Blu-ray (registered trademark) disk), a magneto-optical disk (such as an MO), or a flash memory (such as an SD card, a USB memory, or an SSD). In the alternative, the physiological information processing program which is stored in the storage medium may be installed in the storage device 3. Then, the program which is installed in the storage device 3 may be loaded in the RAM, and thereafter the processor may execute the program which is loaded in the RAM. In this way, the physiological information processing method of the embodiment is executed by the processing apparatus 1.

The physiological information processing program may be downloaded from a computer on a communication network, through the network interface 4. Also in the alternative, the downloaded program may be installed in the storage device 3.

Although the embodiment of the presently disclosed subject matter has been described, the technical scope of the presently disclosed subject matter should not be limitedly interpreted by the description of the embodiment. It should be understood by those skilled in the art that the embodiment is a mere example, and may be variously changed within the scope of the presently disclosed subject matter as defined in the claims. The technical scope of the presently disclosed subject matter should be determined based on the scope of the presently disclosed subject matter as defined in the claims, and the scope of equivalence thereof.

What is claimed is:

1. A method for processing physiological information, the method comprising:
   acquiring electrocardiogram data from a subject;
   acquiring pulse wave data from the subject;
   measuring a plurality of RR intervals based on the acquired electrocardiogram data;
   measuring a plurality of pulse wave transit times based on the acquired electrocardiogram data and the acquired pulse wave data;
   calculating, based on the measured RR intervals and the measured pulse wave transit times during a given time period, a coefficient parameter indicating a correlation coefficient between the measured RR intervals and the measured pulse wave transit times; and
   controlling an administration of fluid to the subject to stop when the calculated coefficient parameter exceeds a threshold value.

2. The method of claim 1 further comprising:
   determining whether the calculated parameter exceeds a given threshold or not; and
   stopping the administration of fluid to the subject when the calculated parameter exceeds the given threshold.

3. The method of claim 1, wherein the parameter includes a correlation coefficient between the RR intervals and the pulse wave transit times.

4. The method of claim 1, wherein the parameter includes a gradient of a regression line indicating correlation between the RR intervals and the pulse wave transit times.

5. The method of claim 1, wherein the method is performed by a computer.

6. The method of claim 1, wherein each of the plurality of pulse wave transit times indicates a time interval from a peak point of an R wave of the acquired electrocardiogram to a rising point of a pulse waveform that appears next to the R wave.

7. A computer readable storage medium storing a program causing a computer to execute a process for processing physiological information, the process comprising:
   acquiring electrocardiogram data from a subject;
   acquiring pulse wave data from the subject;
   measuring a plurality of RR intervals based on the acquired electrocardiogram data;
   measuring a plurality of pulse wave transit times based on the acquired electrocardiogram data and the acquired pulse wave data;
   calculating, based on the measured RR intervals and the measured pulse wave transit times during a given time period, a coefficient parameter indicating a correlation coefficient between the measured RR intervals and the measured pulse wave transit times; and
   controlling an administration of fluid to the subject to stop when the calculated coefficient parameter exceeds a threshold value.

8. A physiological information processing apparatus comprising:
   a processor; and
   a memory configured to store computer readable instructions,
   wherein, when the computer readable instructions are executed by the processor, the physiological information processing apparatus performs:
   acquiring electrocardiogram data from a subject;
   acquiring pulse wave data from the subject;
   measuring a plurality of RR intervals based on the acquired electrocardiogram data;
   measuring a plurality of pulse wave transit times based on the acquired electrocardiogram data and the acquired pulse wave data;
   calculating, based on the measured RR intervals and the measured pulse wave transit times during a given time period, a coefficient parameter indicating a correlation coefficient between the measured RR intervals and the measured pulse wave transit times; and
   controlling an administration of fluid to the subject to stop when the calculated coefficient parameter exceeds a threshold value.

9. The physiological information processing apparatus according to claim 8, wherein, when the computer readable instructions are executed by the processor, the physiological information processing apparatus further performs:
   determining whether the calculated parameter exceeds a given threshold or not, and
   stopping the administration of fluid to the subject when the calculated parameter exceeds the given threshold.

10. The physiological information processing apparatus according to claim 8, wherein the parameter is a correlation coefficient between the plurality of RR intervals and the plurality of pulse wave transit times.

11. The physiological information processing apparatus according to claim 8, wherein the parameter includes a gradient of a regression line indicating correlation between the plurality of RR intervals and the plurality of pulse wave transit times.

12. The method of claim 1, further comprising:
   outputting the calculated parameter.

13. The method of claim 1, further comprising:
   determining whether the calculated parameter exceeds a given threshold or not; and
   outputting information indicating that the calculated parameter exceeds the given threshold.

14. The physiological information processing apparatus according to claim 8, wherein, when the computer readable instructions are executed by the processor, the physiological information processing apparatus further performs:
   outputting the calculated parameter.

15. The physiological information processing apparatus according to claim 8, wherein, when the computer readable instructions are executed by the processor, the physiological information processing apparatus further performs:
   determining whether the calculated parameter exceeds a given threshold or not; and
   outputting information indicating that the calculated parameter exceeds the given threshold.

16. The physiological information processing apparatus according to claim 8, wherein each of the plurality of pulse wave transit times indicates a time interval from a peak point of an R wave of the acquired electrocardiogram to a rising point of a pulse waveform that appears next to the R wave.

17. A method for processing physiological information, the method comprising:
   acquiring electrocardiogram data from a subject;
   acquiring pulse wave data from the subject;

measuring a plurality of RR intervals based on the acquired electrocardiogram data;

measuring a plurality of pulse wave transit times based on the acquired electrocardiogram data and the acquired pulse wave data;

displaying, on a display, a graph of a relationship between the RR intervals and the pulse wave transit times, wherein a first axis of the graph corresponds to the RR interval at a time i, and a second axis of the graph corresponds to the pulse wave transit time at a time i+1;

calculating, based on the measured RR intervals and the measured pulse wave transit times during a given time period, a parameter related to a correlation between the measured RR intervals and the measured pulse wave transit times; and outputting the calculated parameter on the display and changing a visual mode of the display based on a value of the calculated parameter when the calculated parameter exceeds a threshold value, wherein the parameter includes a correlation coefficient between the RR intervals and the pulse wave transit times or a gradient of a regression line indicating the correlation between the RR intervals and the pulse wave transit times.

18. The method of claim 17, wherein each of the plurality of pulse wave transit times indicates a time interval from a peak point of an R wave of the acquired electrocardiogram to a rising point of a pulse waveform that appears next to the R wave.

\* \* \* \* \*